United States Patent
Moberg et al.

(10) Patent No.: US 8,551,042 B2
(45) Date of Patent: Oct. 8, 2013

(54) TIP WITH CAVITY FOR RADIOPAQUE FILED ADHESIVE

(75) Inventors: John R. Moberg, Elk River, MN (US); Michael Gerdts, Big Lake, MN (US); Leah Tilstra, Ramsey, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2137 days.

(21) Appl. No.: 11/224,416

(22) Filed: Sep. 12, 2005

(65) Prior Publication Data

US 2007/0078387 A1    Apr. 5, 2007

(51) Int. Cl.
*A61M 29/00* (2006.01)

(52) U.S. Cl.
USPC .......................................... 604/103; 604/529

(58) Field of Classification Search
USPC ................................................ 604/103, 533
See application file for complete search history.

(56) References Cited

U.S. PATENT DOCUMENTS

| | | | | |
|---|---|---|---|---|
| 4,645,490 A | * | 2/1987 | Rosenberg | 604/103 |
| 4,817,613 A | | 4/1989 | Jaraczewski et al. | 128/658 |
| 5,045,072 A | | 9/1991 | Castillo et al. | 604/280 |
| 5,630,794 A | * | 5/1997 | Lax et al. | 604/22 |
| 5,876,376 A | * | 3/1999 | Schwab et al. | 604/103 |
| 6,171,297 B1 | | 1/2001 | Pedersen et al. | 604/527 |
| 6,447,462 B1 | * | 9/2002 | Wallace et al. | 600/561 |
| 6,623,504 B2 | | 9/2003 | Vrba et al. | 606/192 |
| 6,652,507 B2 | | 11/2003 | Pepin | 604/523 |
| 6,931,194 B2 | * | 8/2005 | Dowd et al. | 385/135 |

* cited by examiner

*Primary Examiner* — Kevin C Sirmons
*Assistant Examiner* — Deanna K Hall
(74) *Attorney, Agent, or Firm* — Vidas, Arrett & Steinkraus, P.A.

(57) ABSTRACT

A catheter tip assembly comprises a catheter tip having a fill port and an inner lumen having at least one cavity. The cavity is in communication with the fill port. The cavity is constructed and arranged to receive a radiopaque material through the fill port. The radiopaque material adhesively engages the catheter tip to a catheter.

21 Claims, 9 Drawing Sheets

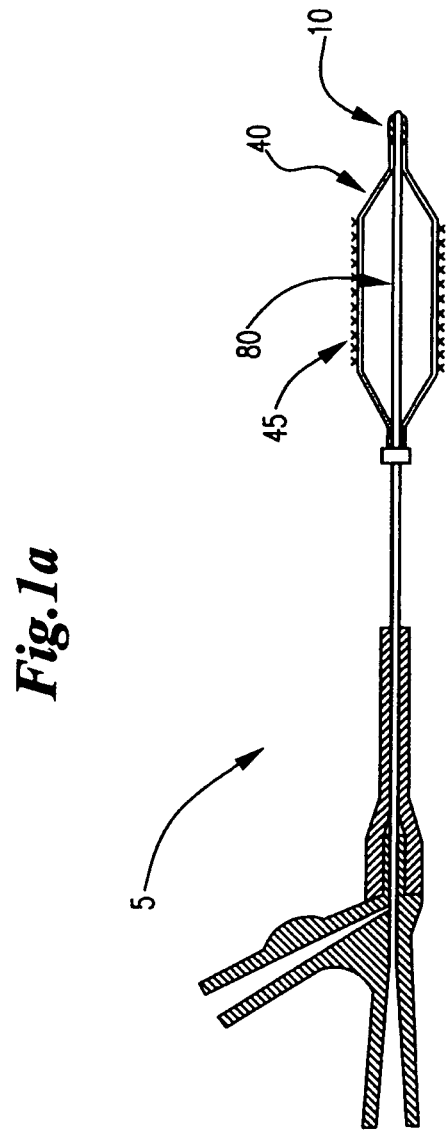

TIP WITH CAVITY FOR RADIOPAQUE FILED ADHESIVE

BACKGROUND OF THE INVENTION

This invention relates generally to catheters, and more specifically to assemblies and methods that may be used for delivering and deploying one or more implantable medical devices including, without limitation: stents, grafts, stent-grafts, vena cava filters, expandable frameworks, etc., hereinafter referred to collectively as stents, within a body lumen.

When advancing a catheter through a body lumen radiopaque marker bands are sometimes located within the vicinity of the catheter tips or medical device in order to better locate the position of the catheter during a medical procedure.

It is known that the marker bands provided on some catheters tend to increase the profile of the catheter, often undesirably. The marker bands may also become dislodged or shifted, which can give false readings on the location of one or more portions of the catheter such as the medical device receiving region, the distal region, etc. It would be desirable to provide a catheter whose position can be located during a procedure without the addition of marker bands.

The art referred to and/or described above is not intended to constitute an admission that any patent, publication or other information referred to herein is "prior art" with respect to this invention.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

SUMMARY OF THE INVENTION

In at least one embodiment, a catheter tip assembly may comprise a tubular member, catheter tip, bumper, etc., that defines a fill port and an inner lumen having at least one cavity for receipt of a radiopaque substance. In at least one embodiment, the at least one cavity may be in communication with the fill port. In at least one embodiment, the cavity may be constructed and arranged to receive a radiopaque material through the fill port. In at least one embodiment, the radiopaque material may adhesively engage the tubular member to a catheter shaft.

In at least one embodiment, the catheter tip and catheter are engaged by a radiopaque adhesive having a first state and a second state. In at least one embodiment, the adhesive is flowable in the first state and in the second state the adhesive is in a non-flowable state, which acts to adhesively secure the catheter tip to the catheter shaft, but wherein the adhesive remains flexible enough so as to not inhibit tip performance. In at least one embodiment for example the radiopaque adhesive has a shore D hardness from 40 to 55 D when in the second or non-flowable state.

In at least one embodiment, the radiopaque adhesive is characterized as having only a flowable state under normal conditions.

In at least one embodiment, at least one portion of the catheter tip is constructed and arranged to engage a catheter shaft such that an interference seal is formed between the inner surface and catheter shaft. In at least one embodiment, the interference seal can be formed such that material within the cavity is prevented from traveling into other portions of the inner lumen.

In at least one embodiment, the catheter tip assembly defines an air vent. In at least one embodiment, the air vent is a hole which passes through the outer surface and catheter tip wall and into the cavity to improve adhesive flow. In at least one embodiment, the hole radially passes through the outer surface and catheter tip wall and into the cavity to improve adhesive flow.

In at least one embodiment, the catheter tip assembly may include an inner lumen of the catheter tip which tapers such that the inner lumen at one location has a greater diameter than the inner lumen at another location.

In at least one embodiment, the at least one interference seal is a slidable seal.

In at least one embodiment, the catheter tip assembly may include a catheter tip having a plurality of fill ports.

In at least one embodiment, the catheter tip assembly may include a catheter tip selected from the group consisting of thermoplastic polyurethane (e.g. Pellethane™, etc.), polyolefin, silicone, or any combination thereof.

In at least one embodiment, a catheter tip assembly may comprise a catheter tip having an inner lumen. In at least one embodiment, the inner lumen may be constructed and arranged such that a layer of radiopaque adhesive can be applied to the inner lumen and affix the catheter tip to a catheter positioned within the inner lumen.

These and other embodiments of the invention are pointed out with particularity in the claims annexed hereto and forming a part hereof. However, for additional understanding of the invention, its advantages and objectives obtained by its use, reference should be made to the drawings which form a further part hereof and the accompanying descriptive matter, in which there is illustrated and described various embodiments of the invention.

BRIEF DESCRIPTION OF THE SEVERAL VIEWS OF THE DRAWING(S)

A detailed description of the invention is hereafter described with specific reference being made to the drawings.

FIG. 1a illustrates a cross-sectional side view of a catheter assembly with a catheter tip.

DETAILED DESCRIPTION OF THE INVENTION

Figure 1B:
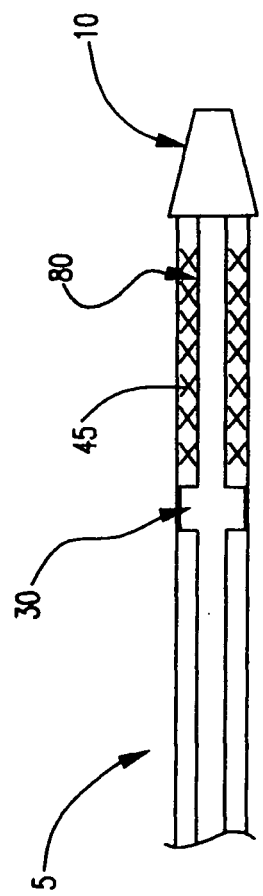
FIG. 1b illustrates a cross-sectional side view of a distal portion of a catheter assembly with a catheter tip and a medical device bumper.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Referring generally to FIG. 1a, a cross-sectional side view of a catheter tip assembly 10 is shown. The catheter tip assembly 10 is mounted on catheter shaft 80 of a catheter 5. As shown in FIG. 1b, a medical device bumper 30 for a self expanding medical device 45 may also be disposed about the catheter shaft 80. The medical device bumper can longitudinally abut the catheter balloon 40. An implantable medical device 45 such as a stent can be positioned adjacent to or abut the medical device bumper prior to delivery.

In regard to FIGS. 1a and 1b, it is noted that embodiments of the present invention incorporate a variety of catheter configurations, which may or may not include a balloon or other expandable member.

The catheter tip 10 and/or bumper 30 can be mounted on the catheter using an adhesive having a radiopaque material (eg., UV adhesives, 2 part epoxies, etc.). The radiopaque material can then be fluoroscopically located during a procedure.

Figure 2:
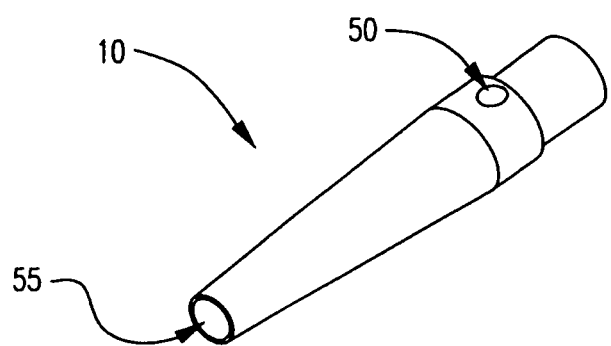
FIG. 2 is a perspective view of a catheter tip.
Figure 3:
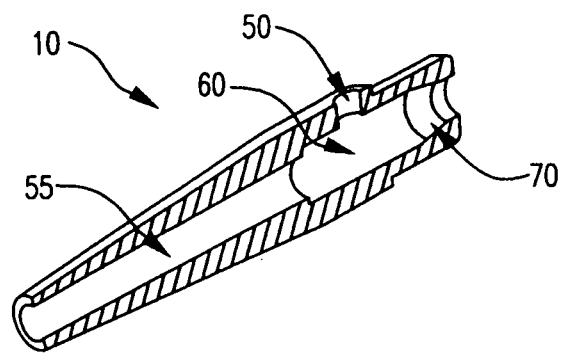
FIG. 3 illustrates a cross-sectional perspective side view of a catheter tip.

In FIG. 2 a perspective view of an inventive catheter tip 10 is shown. The catheter tip 10 has a fill port 50 that is in fluid communication with inner lumen 55. A portion of the inner lumen 55 comprises cavity 60, as shown in FIG. 3. The cavity has a diameter substantially greater than other portions of the inner lumen. A radiopaque material may be injected or otherwise positioned within the cavity 60 through the fill port 50 so as to provide the tip with a radiopaque region which maintains a low profile of the catheter, and without the need to employ extraneous marker bands.

In at least one embodiment, the radiopaque material can be an adhesive having a radiopaque material therein. The adhesive may have a flowable state suitable for injecting the material into the cavity 60 via the fill port 50 and/or a non-flowable state.

In at least one embodiment when the material is in the non-flowable state the material acts to adhesively or otherwise engage the tip 10 to the catheter shaft 20. In at least some embodiments the material in the non-flowable state remains flexible enough to allow the tip to track through the tortuous confines of a body lumen or vessel without adverse affects to the lumen or vessel wall. Depending on the composition of the material 90, the flexibility and/or stiffness of the tip 10 may be selected or modified to provide for improved tracking, pushing and/or other characteristics.

As previously described, in at least one embodiment, material 90 is imparted with a radiopaque aspect, which may be provided by combining an adhesive material with one or more radiopaque substances. Examples of radiopaque material include but are not limited to are barium sulfate, tungsten, gold and/or platinum. All of which may be in the form of a powder.

FIG. 3 is a cross-sectional view of an inventive catheter tip 10 having fill port 50 which is in communication with cavity 60. Cavity 60 is constructed and arranged to accommodate a catheter shaft as well as an adhesive; the adhesive affixing the catheter tip to the catheter shaft. A draft portion 70 of the cavity 60 in this embodiment has a frusta-conical shape and assists in under cut core pin removal. In some embodiments, the further the shaft is advanced in a distal direction, the tighter the seal will be around the shaft.

Figure 4:
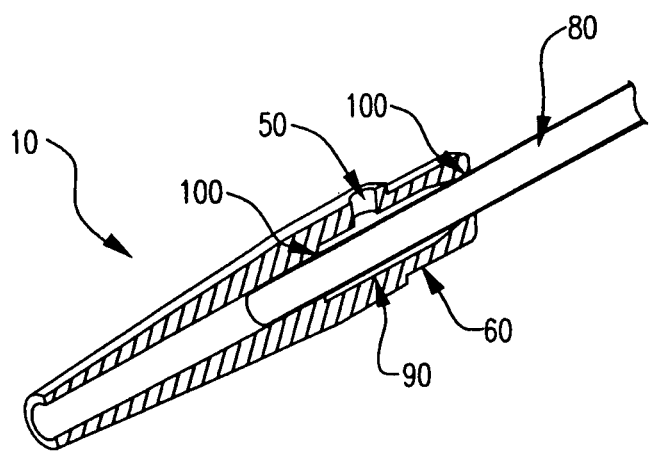
FIG. 4 illustrates a cross-sectional perspective side view of a catheter tip mounted on a catheter.

In FIG. 4 a catheter shaft 80 is inserted within the catheter tip 10. In at least one embodiment, the cavity 60 is the portion of the inner lumen in communication with fill port 50 and not completely filled by the catheter shaft 80. Radiopaque loaded adhesive 90 at least partially fills the cavity 60 about the catheter shaft 80 and affixes the catheter tip 10 to the catheter shaft 80. The location of the adhesive can be confined through the use of interference seals which can be found at seal location 100.

Throughout the remainder of the application "interference seal" will refer to the location where a seal is made when the catheter shaft is inserted. It should be understood that in some instances the seal is made due to the snug fit between the inner lumen and an inserted catheter shaft, but that annular protrusions from the catheter tip wall (even when not illustrated) can also augment the seal at the interference seal locations while in some instances the annular protrusions are necessary for a suitable seal. The seals 100 can movably engage the catheter shaft 80 while preventing adhesive migration between the seals 100 and catheter shaft 80. It should be noted, that in some embodiments there is only one interference seal. In the embodiment of FIG. 4, the catheter tip 10 can be constructed and arranged such that one end of the cavity 60 is limited by a wall which in part forms an interference seal, as shown at the distal interference seal 100 of FIG. 4 or the diameter of the cavity at one end can gradually change till it abuts the interference seal as shown at the proximal interference seal 100 of FIG. 4.

Figure 5:
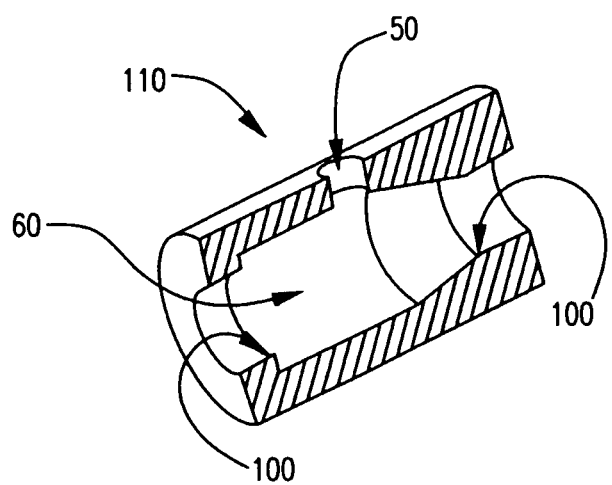
FIG. 5 illustrates a cross-sectional perspective side view of an embodied medical device bumper.
Figure 6:
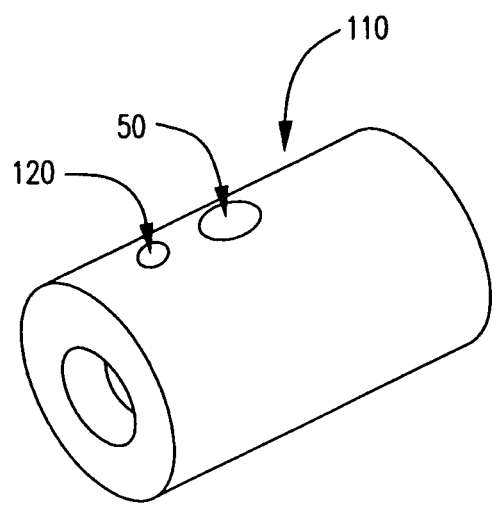
FIG. 6 illustrates a perspective side view of an embodied medical device bumper.

The radiopaque adhesive can also be used in medical device bumpers 110 as shown in FIGS. 5 and 6. The bumpers 110 can be affixed to the catheter shaft in manner similar to that of the catheter tips. Radiopaque adhesive can be introduced into the fill port 50 such that bumper 110 is affixed to the catheter. Interference seals 100 contain the travel of the adhesive when the interference seals form a seal with a catheter shaft.

Figure 7:
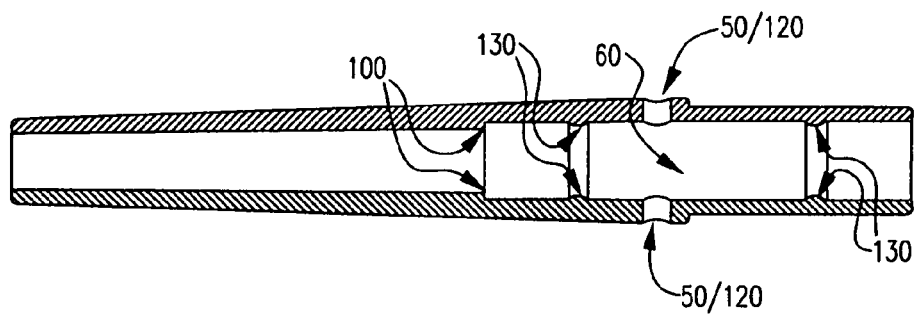
FIG. 7 illustrates a cross-sectional side view of an embodied catheter tip.
Figure 8:
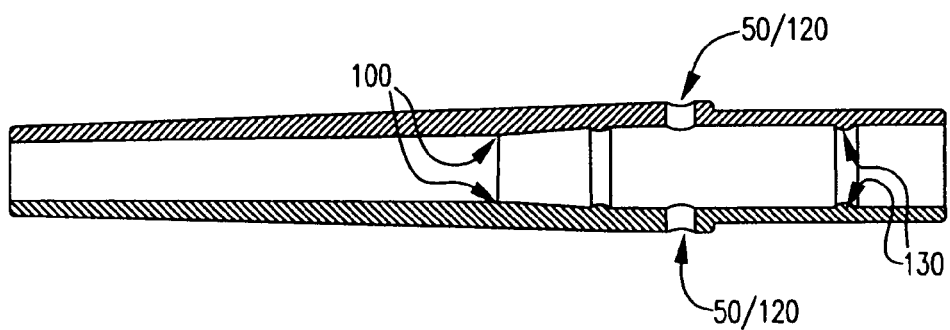
FIG. 8 illustrates a cross-sectional side view of an embodied catheter tip.

It should be noted that the catheter tips and bumpers can have additional fill ports 50 as illustrated in the catheter tips of FIGS. 7-8. In some embodiments adhesive is introduced into the additional fill ports 50. It should be further noted that the additional fill ports can also serve as an air vent 120.

An air vent 120 can be added to improve flow of the adhesive about the catheter shaft 80. The air vent can pass through the wall of the catheter tip and into the cavity 60. The air vent 120 can be smaller than the fill port 50. The air vent need not be opposite the fill port; in some embodiments the air vent 120 is placed close to the fill port 50 as shown in FIG. 6.

In FIGS. 7-8 interference seals can be in the form of annular protrusions 130 that extend from the catheter tip wall. The annular protrusions may be in addition to the interference seals 100 as illustrated in FIG. 4. The bumpers and catheter tips can have the same features about the cavity portion.

In some embodiments, the catheter tips and bumpers do not have a cavity as described in FIGS. 1-8. Rather, in some embodiments, the catheter tips and/or bumpers are constructed and arranged with a larger interior diameter. The larger interior diameter in some embodiments does not have different portions with different inner diameters. In affixing the catheter tip or bumper to the catheter, the larger diameter allows for the use of thicker radiopaque adhesives. This can improve its visibility under fluoroscopy.

In at least one embodiment, the catheter tip and the bumpers are constructed of any suitable material, such as polyesters and copolymers thereof such as those sold including polyalkylene terephthalates such as polyethylene terephthalate (PET) and polybutylene terephthalate (PBT) available under the tradename of EKTAR® available from Eastman Chemical Co. in Kingsport, Tenn., polycyclohexylene terephthalate (PCT); poly(trimethylene terephthalate) (PTT), PCTG and poly(cyclohexanedimethanol-co-ethylene terephthalate) (PETG) copolyesters available under the tradename of EASTAR® available from Eastman Chemical Co., PCTA available under the tradename of DURASTAR® available from Eastman Chemical Co., poly(ethylene naphthalate) (PEN) polyester available from DuPont in Wilmington, Del. under the tradename of TEONEX®; and so forth; polyester elastomers (PEELs); polyamides such as amorphous nylon and nylon 12 such as those available from Elf Atochem under the tradename of CRISTAMID® and copolymers thereof such as GRILAMID® TR-55-LX nylon 12 polyether-block-amide available from EMS-American Grilon in Sumter, S.C.; polyetherimides available from GE Plastics under the tradename of ULTEM®; polystyrene and expandable polystyrene (EPS); acrylonitrile-butadiene-styrene (ABS); styrene-acrylonitrile (SANs); polyphenylene sulfide (PPS); polyphenylene oxides (PPO); interpolymers of PPO and EPS; polyetherketones (PEEK); polyolefins such as polyethylenes and polypropylenes including low, medium and high densities such as HDPE available under the tradename of ALATHON® from Equistar Chemicals; amorphous polyolefins; polyether-block-amides such as those sold under the tradename of PEBAX® available from Elf Atochern; polyimides; polyurethanes; polycarbonates; polyethers; silicones; as well as any copolymers thereof. The above list is intended for illustrative purposes only, and is not intended to limit the scope of the present invention. One of ordinary skill in the art has knowledge of such polymeric materials.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of various embodiments of the invention. Those skilled in the art may recognize other equivalents to the specific embodiment described herein which equivalents are intended to be encompassed by the claims attached hereto.

The invention claimed is:

1. A catheter tip assembly comprising:
a catheter tip having an outer surface and an inner surface with a catheter tip wall therebetween, the inner surface defining an inner lumen having at least one cavity, a fill port passing through the inner and outer surfaces and in communication with the at least one cavity, the at least one cavity constructed and arranged to receive a radiopaque material through the fill port, the catheter tip is disposed about and engaged to a catheter shaft having an outer surface and an inner surface, the outer surface of the catheter shaft forming an interference fit with the inner surface of the catheter tip such that material disposed within the at least one cavity is retained only within the at least one cavity.

2. The catheter tip assembly of claim 1 wherein the radiopaque material adhesively engages the catheter tip to a catheter.

3. The catheter tip assembly of claim 1 wherein the catheter tip and catheter are engaged by a radiopaque adhesive having a first state and a second state, in the first state the adhesive is in a flowable state, in the second state the adhesive is in a non-flowable state.

4. The catheter tip assembly of claim 3 wherein the adhesive in the non-flowable state has a shore D hardness from 40 to 55 D.

5. The catheter tip assembly of claim 1 wherein at least one portion of the catheter tip is constructed and arranged to engage a catheter shaft such that an interference seal is formed between the inner surface and catheter shaft, the interference seal constructed and arranged such that material within the at least one cavity is prevented from traveling into other portions of the inner lumen.

6. The catheter tip assembly of claim 1 wherein the catheter tip wall defines an air vent, the air vent being a hole which radially passes through the outer surface and catheter tip wall and into the at least one cavity to improve adhesive flow.

7. The catheter tip assembly of claim 1 wherein the inner lumen of the catheter tip tapers from one location of greater diameter to another location of lesser diameter.

8. The catheter tip assembly of claim 5 wherein the interference seal is a slidable seal.

9. The catheter tip assembly of claim 1 affixed to a catheter.

10. The catheter tip assembly of claim 1 wherein the catheter tip has a plurality of fill ports.

11. The catheter tip assembly of claim 1 wherein the catheter tip is selected from the group consisting of pellethane, polyolefin, silicone, or any combination thereof.

12. A catheter assembly comprising:
at least one tubular member having an outer surface and an inner surface with a wall therebetween, the at least one tubular member defining a fill port and an inner lumen having at least one cavity, the at least one cavity being in communication with the fill port, the at least one cavity constructed and arranged to accept an adhesive for attaching the at least one tubular member to a catheter, the adhesive comprising at least one radiopaque material;
the at least one tubular member disposed about and engaged to a second tubular member, the second tubular member having an inner surface and an outer surface, the outer surface of the second tubular member forming an interference fit with the inner surface of the at least one tubular member such that material disposed within the at least one cavity is retained only within the at least one cavity.

13. The catheter assembly of claim 12 wherein the at least one tubular member is a catheter tip or stent bumper.

14. The catheter assembly of claim 12 having an air vent, the air vent being a hole which radially passes through the outer surface and wall and into the at least one cavity to improve adhesive flow.

15. The catheter assembly of claim 12 wherein at least one portion of the tubular member is constructed and arranged to engage a catheter shaft such that an interference seal is formed between the inner surface and catheter shaft, the interference seal formed such that material within the at least one cavity is prevented from traveling into other portions of the inner lumen.

16. The catheter assembly of claim 15 wherein the interference seal is a slidable seal.

17. The catheter assembly of claim 12 wherein the tubular member has a plurality of fill ports.

18. The catheter assembly of claim 12 wherein the catheter tip is selected from the group consisting of thermoplastic polyurethane, polyolefin, silicone, or any combination thereof.

19. The catheter assembly of claim 12 affixed to a catheter.

20. The catheter assembly of claim 12 wherein the tubular member and catheter are engaged by a radiopaque adhesive having a first state and a second state, in the first state the adhesive is in a flowable state, in the second state the adhesive is in a non-flowable state.

21. The method of assembling a catheter the method comprising the steps of:
   providing a catheter tip defining a fill port, the catheter tip having an inner surface defining an inner lumen having at least one cavity, the cavity being in communication with the fill port;
   engaging the catheter tip to a catheter shaft outer surface wherein the inner surface of the catheter tip forms an interference fit with the catheter shaft outer surface; and
   filling the at least one cavity via the fill port with a radiopaque material, the radiopaque material adhesively engaging the catheter tip to the catheter shaft.

* * * * *